United States Patent [19]

Quate et al.

[11] Patent Number: 5,319,977
[45] Date of Patent: Jun. 14, 1994

[54] NEAR FIELD ACOUSTIC ULTRASONIC MICROSCOPE SYSTEM AND METHOD

[75] Inventors: Calvin F. Quate, Stanford; Butrus T. Khuri-Yakub, Palo Alto; Shinya Akamine, Stanford; Babur B. Hadimioglu, Mountain View, all of Calif.

[73] Assignee: The Board of Trustees of the Leland Stanford Junior University, Stanford, Calif.

[21] Appl. No.: 718,234

[22] Filed: Jun. 20, 1991

[51] Int. Cl.⁵ .................... G01N 29/06; G01N 29/08; G01N 29/24
[52] U.S. Cl. ............................ 73/606; 73/620; 250/306; 310/336; 324/629; 324/649; 324/662
[58] Field of Search ............... 73/105, 618, 620, 606, 73/579, 630; 250/306; 310/336; 324/629, 649, 662

[56] References Cited

U.S. PATENT DOCUMENTS

| | | | |
|---|---|---|---|
| 4,126,036 | 11/1978 | Nilan et al. | 73/105 |
| 4,646,573 | 3/1987 | Stoll | 73/606 |
| 4,726,229 | 2/1988 | Yamamoto et al. | 73/606 |
| 5,003,815 | 4/1991 | Martin et al. | 73/105 |

FOREIGN PATENT DOCUMENTS

8912805 12/1989 World Int. Prop. O. ............ 73/606

*Primary Examiner*—Hezron E. Williams
*Assistant Examiner*—Rose M. Finley
*Attorney, Agent, or Firm*—Flehr, Hohbach, Test, Albritton & Herbert

[57] ABSTRACT

An acoustic microscope assembly for atomic level inspection of a target object includes a cantilever arm with a sharp tip on its lower surface and a zinc oxide piezoelectric thin film on its upper surface. High frequency excitation signals, having a frequency of at least 50 Megahertz, are applied to the piezoelectric thin film so as to generate high frequency acoustic signals that are transmitted through the sharp tip so as to impact on a target object. The assembly can either receive acoustic signals reflected by the target object, or it can receive acoustic signals that have propagated through the target object. One method of using this assembly is to apply a continuous wave signal to the piezoelectric thin film while scanning the target object, and measuring characteristics of the target object at various positions thereof by measuring the resonant frequency of the transmitted high frequency acoustic signals. Other methods include pulsed operation, and combining acoustic measurements with atomic force measurements and/or tunneling current measurements to characterize a target object. The acoustic microscope assembly can also be used for storing information on a substrate, by deforming the substrate at selected positions, and for reading such stored information by determining which positions on a substrate have been deformed.

22 Claims, 7 Drawing Sheets

NEAR FIELD ACOUSTIC ULTRASONIC MICROSCOPE SYSTEM AND METHOD

The present invention relates generally to scanning near field acoustic microscopy, and particularly to very high frequency near field microscopy assemblies for use in microscopy with resolution beyond the diffraction limit, and very high frequency microscopy assemblies which combine the features of near field acoustic microscopy with features of atomic force microscopes, scanning tunneling microscopes, and other measurement modalities.

BACKGROUND OF THE INVENTION

The present invention extends the capabilities of near field acoustic microscopes by (1) using a new scanning probe design, (2) using much higher frequencies than previously used, thereby increasing lateral resolution and making accurate phase measurements possible, and (3) combining the capabilities of near field acoustic microscopy with those of atomic force microscopes, scanning tunneling microscopes, and/or other measurement methods.

Near field acoustic microscopy is one of several microscopy methodologies capable of atomic resolution microscopy. In near field acoustic microscopes the tip of a scanning prove is used to confine acoustic energy at high frequencies to a small diameter equal to that of the tip itself. The tip's diameter is much less than the acoustic wavelength. Acoustic energy quickly spreads out in the lateral direction as the spacing between the tip and a sample is increased. Therefore, in order to realize the full benefit of the confinement of acoustic energy by the narrow tip, it is necessary to observe the sample when it is placed very near the apex of the tip. Hence the name "near field" acoustic microscopy.

There has been previous work in this field. Zieniuk has transmitted sound waves through a narrow tip into water. The waves in the water propagate to the sample and enter the sample with a diameter that is more or less equal to the path length in water. In this situation the lateral resolution is determined by the spacing between the tip and sample. The system is quite inefficient since there is an impedance mismatch between the tip and water, and between the water and sample. J. K. Zieniuk, "Imaging Using Ultrasonic PIN Scanning Microscopy," IEEE Proceedings 1986 Ultrasonics Symposium, edited by B. R. McAvoy, Vol. 2, pp. 1037-1039. See also, W. Durr, D. A. Sinclair and E. A. Ash, "High resolution acoustic probe," Electronic Letters, Vol. 16, pp. 805-806, 1980.

Güthner and Dransfeld have demonstrated a second system by using the sharp corner of a tuning fork. With the tuning fork vibrating at its resonant frequency they brought it near to a sample and determined that the resonant frequency changed in the presence of the sample. The change was proportional to the spacing, and as they translated the sample beneath the tuning fork's corner the spacing would change, due to the topography of the sample's surface. Spacing changes were reflected by the changes in the resonant frequency. See (1) P. Guethner, E. Schreck, K. Dransfeld, "Scanning Tunneling Microscopy and Related Methods," edited by R. J. Behm et al., pp. 507-513 (chapter entitled "Scanning Nearfield Acoustic Microscopy"), Kluwer Academic Publishers, Netherlands 1990; and (2) P. Güthner, U. Ch. Fischer, and K. Dransfeld, "Scanning Nearfield Acoustic Microscopy," Applied Physics and Laser Chemistry, Applied Physics B., pp. 89-92, Springer-Verlag 1989.

Uozumi has demonstrated a system in which a bulk piezoelectric transducer was mounted in back of the tip of a scanning tunneling microscope (STM) and used this to excite sound waves at 1.4 MHz. These waves traveled down to the apex of the tip and returned. Thus, a reflection mode of operation was used. Uozumi found that the magnitude of the reflected signal was dependent on the spacing between the tip and sample. Kiyohiko Uozumi et al., "A Possible Novel Scanning Ultrasonic Tip Microscope," Japanese Journal of Applied Physics Vol. 28, No. Jul. 7, 1989 pp. L 1297-L 1299.

In still another experiment, Takata of Hitachi, Ltd., demonstrated a system where sound was transmitted from the tip through the sample to a piezoelectric detector place on the back side of the sample, thereby using a transmission mode of operation. The frequency used was a few kilohertz. See (1) Keiji Takata et al., "Tunneling acoustic microscope," Appl. Phys. Lett. 55(17), Oct. 23, 1989 pp. 1718-1720; and (2) Keiji Takata et al., "Electrostatic Force Imaging by Tunneling Acoustic Microscopy," Japanese Journal of Applied Physics Vol. 30, No. 2B, February 1991 pp. L 309-L 312.

The previously cited prior art methods for generating ultrasonic sound are cumbersome and inefficient. They are also restricted to low frequencies.

The present invention improves on the prior art acoustic microscopes by providing a scanning probe with a piezoelectric thin film transducer and using significantly higher ultrasonic frequencies, made possible by the use of a piezoelectric thin film instead of bulk piezoelectric transducers. It is desirable to operate a high frequencies, e.g., above 50 MHz, with short wavelengths. The inventors believe that the efficiency, and lateral resolution, of near field acoustic microscopy will improve as shorter and shorter wavelengths are used. Previous experiments have demonstrated that sound can be generated and detected at 100 GHz, with wavelengths in solids near 50 nanometers.

The present invention provides a number of different methods of exciting these high frequency sound waves, and detects the waves after interaction with a sample using a thin film of piezoelectric material such as Zinc oxide. These new modes of operation which expand the utility of acoustic microscopes, and combination AFM-/acoustic microscopes and STM/acoustic microscopes.

SUMMARY OF THE INVENTION

In summary, the present invention is an acoustic microscope assembly for atomic level inspection of a target object. The assembly includes a scanning probe with a sharp tip on its lower surface and a zinc oxide piezoelectric thin film on its upper surface. High frequency excitation signals, having a frequency of at least 50 Megahertz, are applied to the piezoelectric thin film so as to generate high frequency acoustic signals that are transmitted through the sharp tip so as to impact on a target object. The assembly can either receive acoustic signals reflected by the target object, or it can receive acoustic signals that have propagated through the target object.

One method of using this assembly is to apply a continuous wave signal to the piezoelectric thin film while scanning the target object, and measuring characteristics of the target object at various positions thereof by measuring the resonant frequency of the transmitted high frequency acoustic signals. Other methods include pulsed operation, and combining acoustic measurements with atomic force measurements and/or tunneling current measurements to characterize a target object. Acoustic waves can be excited using a wide variety of other techniques, including electromagnetic fields, modulated laser beams, and pulsed resistive or inductive heating. Frequency mixing can also be used to generate ultrasonic signals with multiple frequency components. In all such cases, the physical characteristics of the sample under test will modulate the ultrasonic sound waves. The resulting modulated ultrasonic sound waves are detected using thin film piezoelectric detectors mounted either on a scanning probe or on the sample itself.

The acoustic microscope assembly can also be used for ultrasonic drilling to modify the surface structure of an object in a controlled way. This technique could be used to scribe a line in a soft material such as the polymer films that are used for photoresist. Very high frequency ultrasonic drilling could also be used to store information on a substrate, by deforming the substrate at selected positions, and for reading such stored information by determining which positions on a substrate have been deformed.

BRIEF DESCRIPTION OF THE DRAWINGS

Additional objects and features of the invention will be more readily apparent from the following detailed description and appended claims when taken in conjunction with the drawings, in which:

DESCRIPTION OF THE PREFERRED EMBODIMENT

Since the present invention concerns not only acoustic microscopy but also combinations of acoustic microscopy with AFM and STM, a short description of the physical apparatus used in AFM and STM is provided for those not familiar with this prior art.

AFM and STM operation

Figure 1:
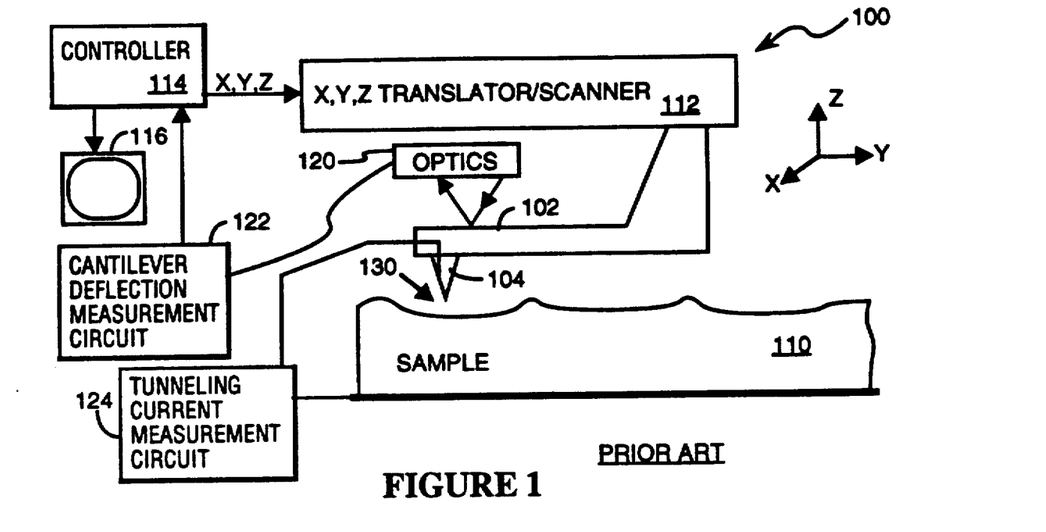
FIG. 1 is a block diagram of an atomic force microscope.

Referring to FIG. 1, there is shown a conceptual diagram of an atomic force microscope 100. A microminiature cantilever arm 102 with a sharp projecting tip 104 at its free end is used to probe the surface of a sample 110. Some atomic force microscopes (AFM's) scan the sample's surface by using an XYZ translator stage 112 to move the cantilever 102 while keeping the sample 110 stationary. In other AFM's the cantilever 102 is kept stationary while an XYZ translator stage moves the sample 110 so as to scan the sample's surface. In the preferred embodiments, a piezoelectric XY translator moves the sample 110, and a separate Z translator moves the cantilever/probe 102 (see FIG. 2). Scanning is controlled by a programmed microcontroller or computer 114, which also analyzes measurement data and displays measurement information on display 116.

The AFM has a "contacting mode" of operation and a "non-contacting mode" of operation. In the "contacting mode" of operation, the tip 104 rides on the surface of a sample with an extremely light tracking force, on the order of $10^{-5}$ to $10^{-10}$N. Profiles of the surface topography are obtained with extremely high resolution. Images showing the position of individual atoms are routinely obtained. In the second non-contacting mode of operation, the tip 104 is held a short distance, on the order of 5 to 500 Angstroms, from the surface of a sample and is deflected by various forces between the sample and the tip; such forces include electrostatic, magnetic, and van der Waals forces. In either mode of operation, measurements of the sample's surface topology or other characteristics are obtained by measuring deflection of the cantilever 102. Deflection of the cantilever is usually measured using precisely aligned optical components 120 coupled to a deflection measurement circuit 122, although other techniques are sometimes used.

Atomic force microscopy is capable of imaging conductive as well as insulating surfaces with atomic resolution. Typical AFM's have a sensitivity of 0.1 Angstrom in the measurement of displacement.

While AFM's and STM's are usually separate devices, for convenience the tunneling current measurement circuitry 124 for a scanning tunneling microscope is also shown in FIG. 1. Convention STMs are used primarily to monitor the electronic character of the surfaces being scanned.

Tunneling currents in conductive or semiconductor samples are induced by placing a conductive tip 104 one to ten Angstroms above the sample, and introducing a low voltage electric field (typically less than one volt) between a conductive tip 104 and the sample, which is mounted on a metal plate for ease of electrical connection to the sample. Tunnelling current, drawn from the tip through the one to ten angstrom gap 130 between the tip 104 and sample 110, is indicative of the size of the gap 130. STMs typically have two modes of operation. The first is constant height mode, for very flat samples, in which the tip is scanned at a constant height and the tunneling current is measured to determine the topography of the sample. The second mode is constant current mode, in which tunneling current is kept constant by varying the height of the cantilever until a preselected current level is restored.

The Near Field Acoustic Microscope Apparatus

Figure 2:
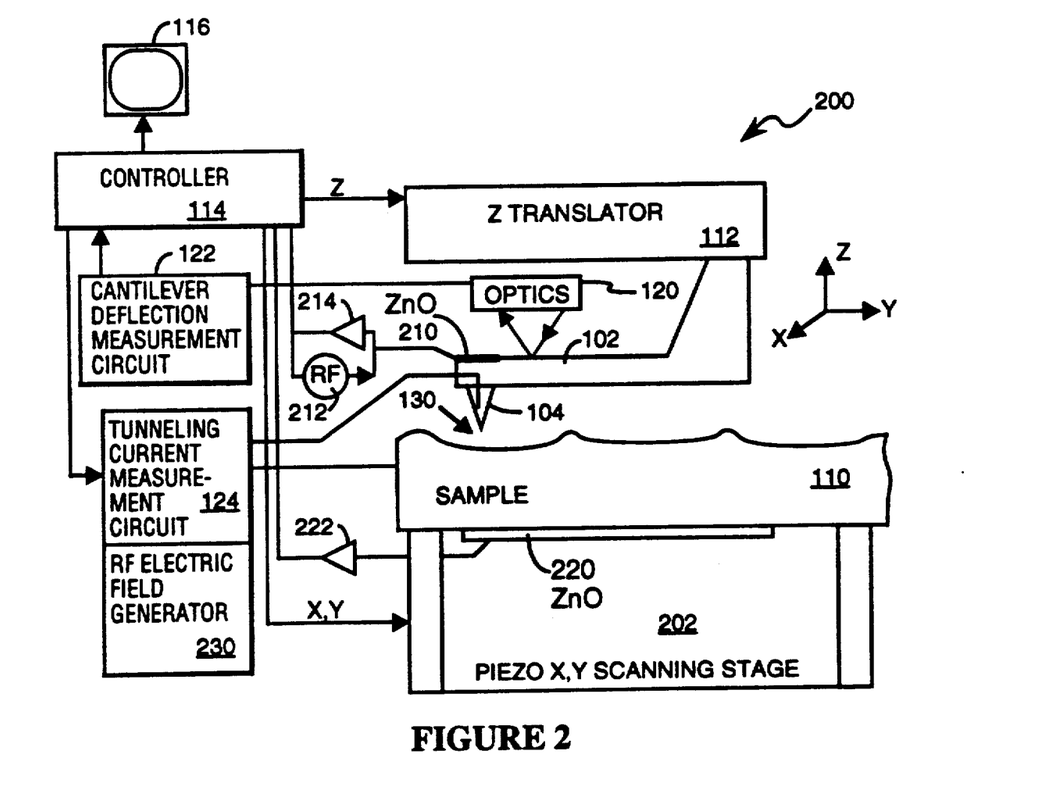
FIG. 2 is a block diagram of an AFM/acoustic microscope in accordance with the present invention.

Referring to FIG. 2, there is show a microscope 200 combining acoustic microscopy and either AFM or STM measurement modalities. Acoustic microscopy is an analysis tool than can be used either alone, or in conjunction with either AFM or STM to analyze the topography and material characteristics of a substrate or other target object. The high frequency waves generated by the present invention can be used to measure material properties at the surface of a sample and just beneath the surface. The microscope is operable with both conducting and insulating surfaces, and can be used to detect impurity atoms in a sample near the surface, such as those place in a sample using ion implantation.

As in FIG. 1, this microscope assembly 200 has a scanning and measurement controller 114, a cantilever 102 with a sharp tip probe 104 positioned over a sample 110, cantilever deflection measurement optics 120 and a cantilever deflection measurement circuit 122 for AFM operation. For STM operation, when the assembly 200 is to be used as an acoustic/scanning tunneling microscope, a tip 104 is provided with a conductive outer layer (e.g., deposited metal), and a tunneling current measurement circuit 124 coupled to the sample and tip detects tunneling currents in the sample 110.

In the preferred embodiments, the sample 110 is mounted on an XY scanning stage 202. This is a "piezo scanning tube" type of stage, which uses piezoelectric actuators to precisely move the sample 110 in the X and Y directions. A separate Z translator apparatus 204 moves the probe 102 up and down relative to the sample 110.

The cantilever 102 has a zinc oxide (ZnO) piezoelectric thin film transducer 210 which has been deposited and patterned on its upper side, in back of the tip 104. Another ZnO piezoelectric thin film transducer 220 can also be formed on the bottom of the sample 110. A very high frequency RF excitation signal generator 212 excites the ZnO transducer 210 with excitation signals at selected frequencies, generally at or above 50 MHz, and preferably above 100 MHz. Detector 214 measures the magnitude and/or phase of acoustic sound waves reflected from the sample 110, and detector 222 measures the magnitude and/or phase of acoustic sound waves transmitted through the sample 110.

For yet another mode of operation, an RF electric field generator 230, coupled to the tip 104 and sample 110 generates high frequency electric fields in the gap 130 between the tip and sample.

There are many modes of operation that can be employed using the present invention. All use a piezoelectric thin film transducer on a probe in back of a sharp tip and/or piezoelectric thin film transducer on the back of the sample 110 under test. In general, each modality generates very high frequency acoustic signals either in or above the sample 110, and then one or both piezoelectric thin film transducers are used to detect those signals and to thereby measure the characteristics of the sample. Those modalities will now be described.

Acoustic Stimulation

The probe tip 104 is scanned over the surface of the sample 110 while positioning the tip's apex a specified distance (e.g., between one and 100 Angstroms) from the sample's surface. For conductive samples, this is typically accomplished by inducing and monitoring tunneling current in the sample 110 using tunneling current measurement circuit 124. For non-conductive samples, this is typically accomplished using atomic force microscopy, using optics 120 and circuit 122 to maintain the tip 104 a specified distance away from the sample's surface.

At selected positions above the sample, RF generator 212 is activated, producing a high frequency excitation signal that stimulates the ZnO thin film transducer 210 above the tip 104. The resulting shock wave acoustic signals pass through the tip's apex 104 and impact on the sample 110. The acoustic sound wave is modulated in a manner that is affected by the sample's topography and physical characteristics. This modulation can be measured using either reflected waves detected by sensor 214 (reflection mode), or by detecting waves transmitted through the sample to ZnO piezoelectric thin film transducer 220 and detected by sensor 222 (transmission mode).

The excitation signal applied to transducer 210 can be either pulses, or a continuous wave signal. Pulsed excitation is often preferred because it allows clear and simple separation of acoustic transmission and reflection signals from the excitation signal. Continuous wave excitation has the advantage that it enables the system to monitor changes in resonance frequency and changes in the sharpness of the frequency response peak (usually referred to as Q), both of which are indicative of the physical properties of the sample under test. The measurements are mapped in accordance with the X, Y position of the probe, enabling the controller 114 to generate tables and/or maps of the sample's properties.

It is noted that if the initial stimulation of the sample is at frequency f1, the non-linearity associated with the coupling across the tip and sample will produce harmonics of the fundamental frequency. The harmonics can be sensed by tuning the sensors to the appropriate frequencies, such as 2×f1 for the second harmonic.

RF Electromagnetic Field Stimulation

Still referring to FIG. 2, in this mode of operation an RF field is generated in the gap 130 between the tip 104 and the sample by RF electric field generator 230. In this mode of operation, the tip 104 must be either made from conductive material (e.g., heavily doped silicon), or be covered with a conductive material such as a sputtered metal layer. The tip and sample form a capacitor with a field $E = V/d$ therebetween, where "V" is the voltage across the gap and "d" is the distance across the gap.

The RF field fluctuates at high frequency, preferably at least 50 MHz. The fluctuating field induces a sound wave into the media with a strain S that is proportional to the square of the electrical field E. The fluctuating strain can be detected by either the piezoelectric film 220 on the back of the sample 110, or by the piezoelectric film 210 on the back of the probe 102. Conductivity of the sample in the region under the tip 104 is measured by monitoring the piezoelectric output signal at twice the frequency of the RF field.

Figure 3:
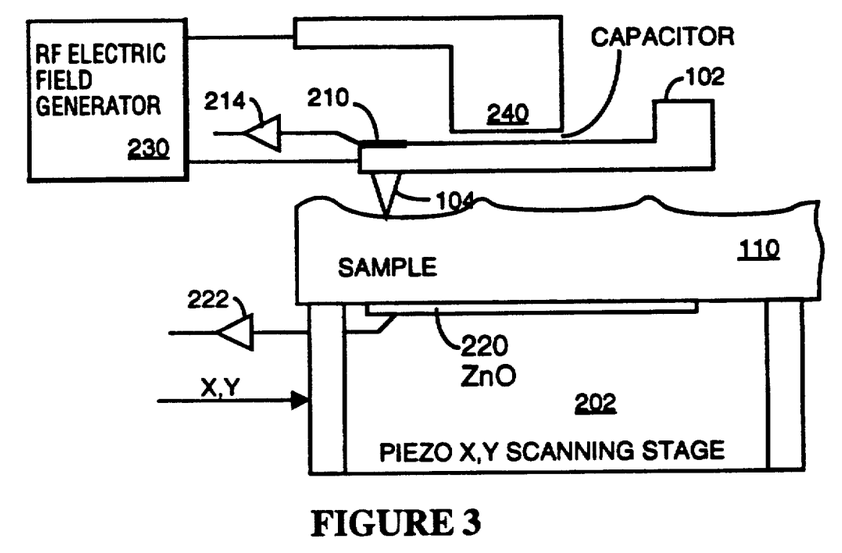
FIG. 3 is a block diagram of an acoustic microscope using an RF electrical field generator to vibrate the microscope's cantilever.

Using the system configuration shown in FIG. 3, with the tip 104 contacting the sample, an RF field is created between a capacitor plate 240 and the cantilever 102 to vibrate the cantilever 102. The resulting ultrasonic waves in the sample, measured via detector 214 or detector 222, are indicative of elastic properties of the sample 110.

Combined Acoustic and RF Electromagnetic Field Stimulation

Figure 4:
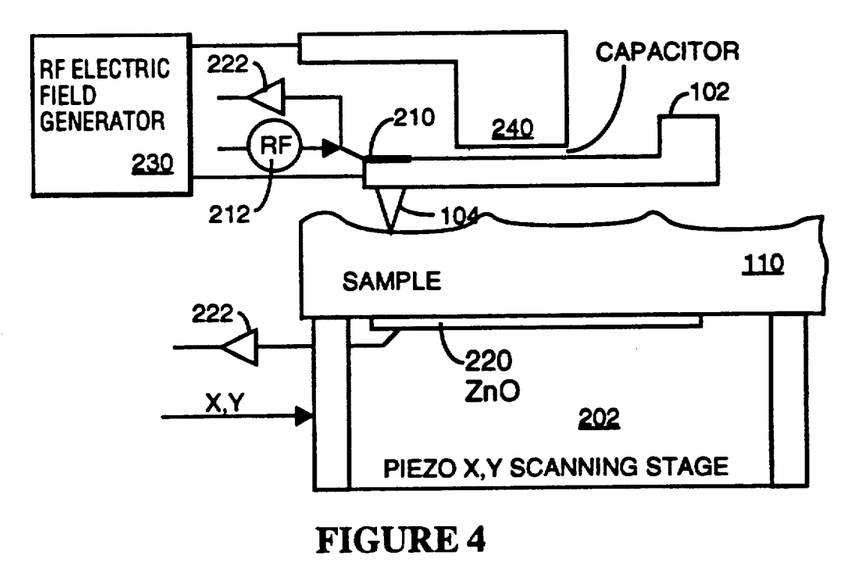
FIG. 4 is a block diagram of an acoustic microscope using an RF electrical field generator to vibrate the microscope's cantilever while also generating ultrasonic sound waves with a piezoelectric thin film transducer.
Figure 5:
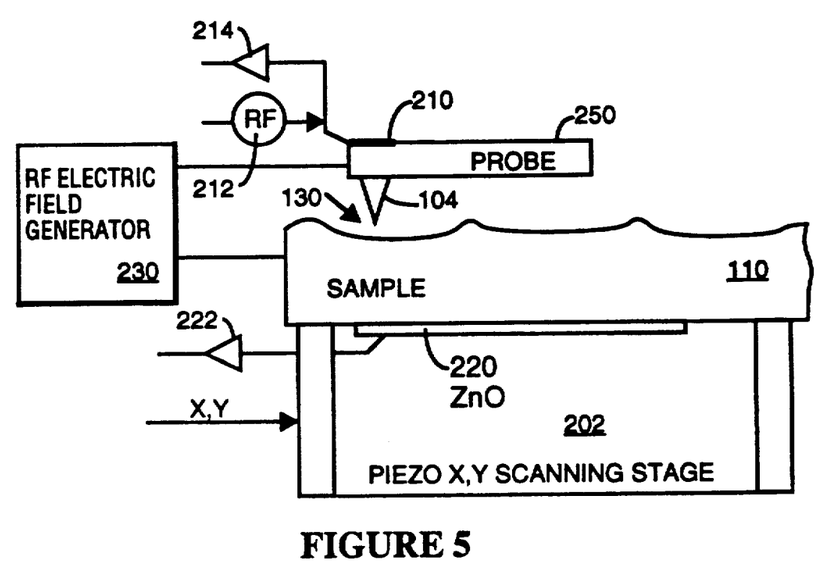
FIG. 5 is a block diagram of an acoustic microscope using an RF electrical field generator to generate an electric field in the gap between a probe and a sample.

FIGS. 4 and 5 show two microscope assemblies which combine acoustic and RF electromagnetic field stimulation. In FIG. 4, the piezoelectric thin film 210 is driven with an RF excitation signal of frequency $\omega 1$. In addition, an RF field of frequency $\omega 2$ is created between a capacitor plate 240 and the cantilever 102 to vibrate the cantilever 102. The two stimuli are applied simultaneously, producing acoustic sound waves in the sample 110 with frequency components at frequencies $\omega 1 \pm 2$, typically detected using transmission mode sensor 222 coupled to the film ZnO piezoelectric transducer 220 on the bottom of the sample 110.

In FIG. 5, the piezoelectric thin film 210 is driven with an RF excitation signal of frequency $\omega 1$, and an RF field of frequency $\omega 2$ is created in the gap 130 between tip 104 and sample 110. Note that in this embodiment, the tip 104 can be mounted on a ordinary scanning probe 250 which is not a cantilever. The two stimuli are applied simultaneously, producing acoustic sound waves in the sample 110 with frequency components at frequencies $\omega 1 \pm 2$, typically detected using transmission mode sensor 222.

In both FIG. 4 and FIG. 5, the sound waves generated in the sample can also be detected with sensor 214 because these sound waves will also propagate through the gap 130, tip 104 and probe 250.

The system of FIG. 4 can be used to excite the cantilever 102 at its resonant frequency $\omega\Delta$, typically around 100 KHz. This resonance will be changed with loading of the tip by proximity to the sample. Simultaneously propagating sound through the sample at frequency $\omega 1$ (e.g., at 100 MHz) by directly exciting the ZnO transducer 210, the system can detect mixing of the two frequencies by monitoring frequencies $\omega 1 \pm \Delta \omega$.

Laser Beam/Surface Heating Stimulation

Figure 6:
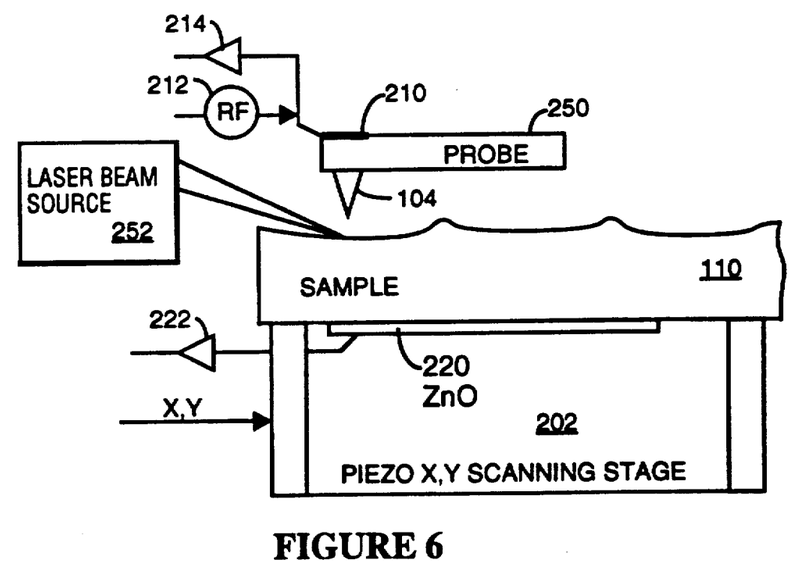
FIG. 6 is block diagram of an acoustic microscope using an amplitude modulated laser beam to generate ultrasonic acoustic sound waves in a sample.

Referring to FIG. 6, a laser beam amplitude modulated at frequency $\omega 2$ is focused on the surface of sample 110 by a laser beam source 252. The sample's surface expands and contracts, in effect modulated by the laser beam, thereby creating acoustic sound waves in the sample 110. The sound waves are detected by either sensor 214 (reflection mode), or sensor 222 (transmission mode).

Alternately, the piezoelectric thin film 210 can be driven with an RF excitation signal of frequency $\omega 1$, while the sample surface is stimulated with a laser beam that is amplitude modulated at frequency $\omega 2$. The two stimuli are applied simultaneously, producing acoustic sound waves in the sample 110 with frequency components at frequencies $\omega 1 \pm \omega 2$, typically detected using transmission mode sensor 222. Similar frequency modulation can also be accomplished by stimulating the sample surface with two amplitude modulated laser beams, one modulated at frequency $\omega 1$ and the other modulated at frequency $\omega 2$.

Other Stimulation Modalities

Figure 7:
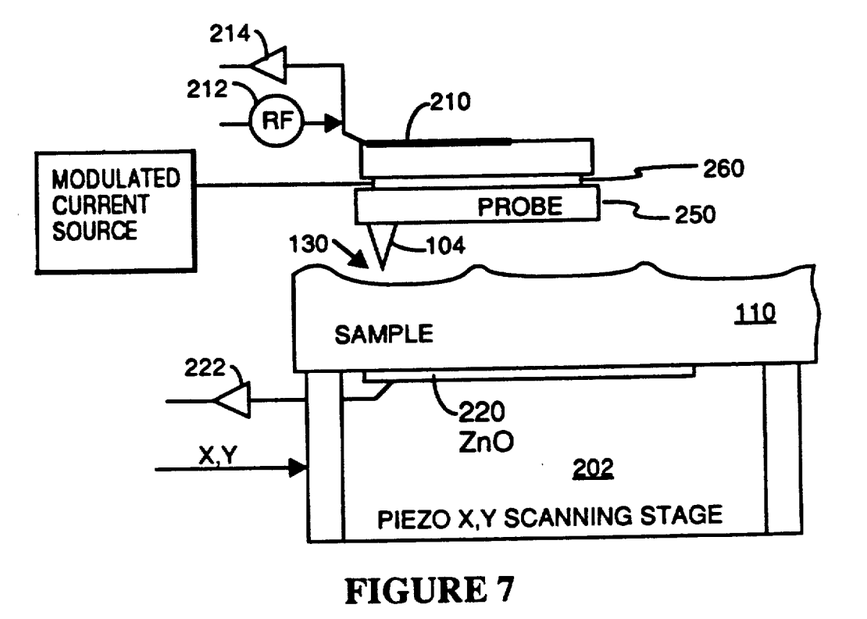
FIGS. 7 and 8 are block diagrams of an acoustic microscope in which resistive films are heated with modulated current to excite acoustic waves in a sample.
Figure 8:
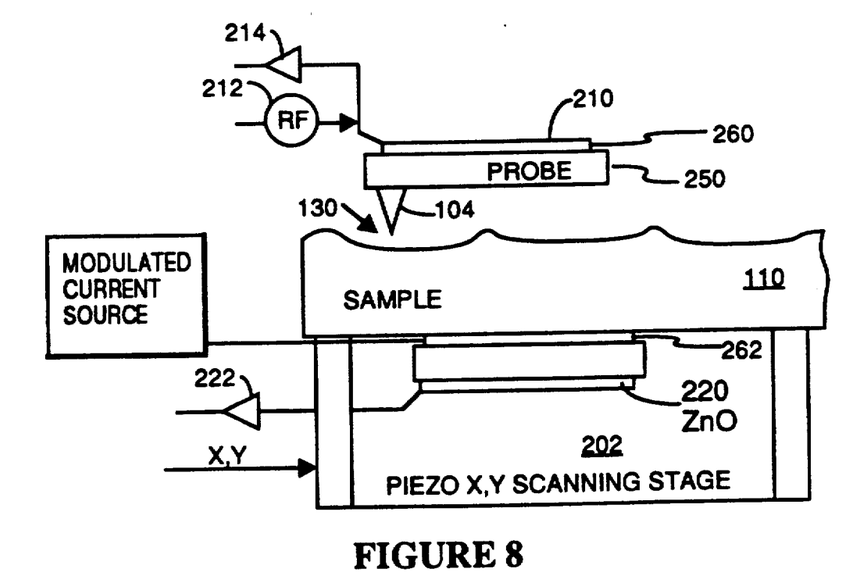
Figure 9:
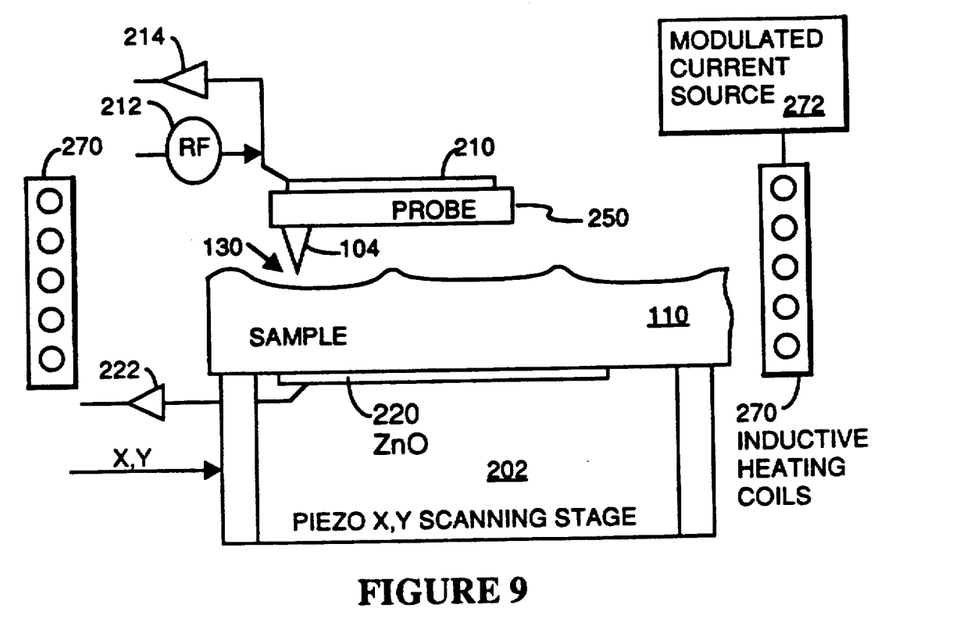
FIG. 9 is a block diagram of an acoustic microscope with inductive heating coils for exciting acoustic waves in a sample.

A number of other stimulation modalities can be used, either alone or in combination with excitation of the ZnO thin film transducer 210 on the probe. These include heating a resistive film 260 on the probe with current modulated at frequency $\omega$ (FIG. 7), or heating a resistive film 262 coupled to the sample with current modulated at frequency $\omega$ (FIG. 8). Modulated heating of the sample could also be accomplished by inductive heating coils 270 with current modulated at frequency $\omega$ (FIG. 9).

In the presence of an RF magnetic field, eddy currents will be induced in the sample if it is conducting, and this periodic heating will induce sound waves in the sample which can be detected with the piezoelectric films.

Figure 10:
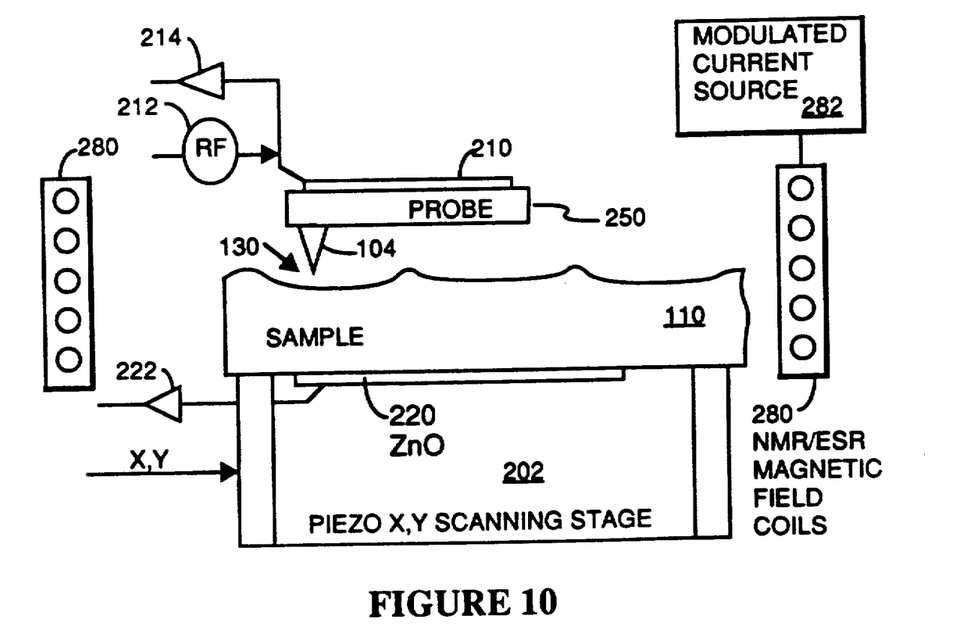
FIG. 10 is a block diagram of an acoustic microscope with magnetic coils for exciting acoustic waves in a sample.

Referring to FIG. 10, the sample 110 may also be stimulated with magnetic fields to induce nuclear magnetic resonance (NMR) or electron paramagnetic resonance (EPR). The NMR/EPR magnetic fields are generated using magnetic field coils 280 driven by a modulated current source 282.

Electron paramagnetic resonance is the process where the spinning electron associated with a given atom undergoes precessional motion in the presence of a magnetic field. The frequency of this precession is determined by the strength of the magnetic field. A magnetic field of 3300 gauss will induce a precessional frequency of $10^{10}$ Hz. The precessional frequency is directly proportional to the magnetic field, so that a field of 30 gauss will induce a precessional frequency of $10^9$ Hz. If we simultaneously apply an external RF electric field with a frequency equal to the precessional frequency, the resonance will greatly magnify the magnitude of the precessional motion. When the RF frequency of the electric field is adjusted to resonance, energy can be absorbed from the external RF source (usually a microwave cavity). This change in energy can be detected in various ways.

Mannassen has detected this resonance by monitoring the changes in the tunneling current in an STM. See Y. Mannassen, R. J. Hamers, J. E. Demuth and A. J. Castellano, Jr., "Direct Observation of the Precessional of Individual Paramagnetic Spins on Oxidized Silicon Surfaces," Phys. Rev. Lett., Vol. 62, P. 2531-2533, May 22, 1989.

The changes in energy can also be detected using the present invention by monitoring changes in acoustic transmission by the sample. The procedure is to apply an RF frequency electrical field from an external source and then slowly change the magnitude of the applied magnetic field (see FIG. 10) until it reaches the resonance value.

In a second variation, the acoustic frequency of an applied acoustic signal (applied via transducer 210) itself can be resonant with the precessional frequency. The EPR signal can be detected without the requirement of an additional external source of RF energy. This system will allow one to detect electron resonance at specific sites in the sample 110 with a resolution determined by the shape of the tip and in turn this will allow one to characterize the sample with a precision that is unavailable with other methods.

Nuclei also possess angular momentum similar to the spinning electron. The significant differences are in the mass of the two entities and the nucleon-nucleon forces which differ from the forces acting on electrons. These differences are reflected in the precessional frequency of the nuclei. With an applied magnetic field of $10^4$ gauss, the resonant frequency is equal to $10^7$ hertz, which is much lower than the electron resonant frequency in the same field. Again, the additional energy absorbed from an external RF source can be detected in the changes in transmission of acoustic energy. The external RF source can be either an electromagnetic field or an acoustic field applied via transducer 210.

NMR is important since the precessional frequency is determined by the chemical nature of the precessing atom. Thus, we can identify the atom species under the tip 104 by measuring the resonant frequency of the precessing nuclei, i.e., by measuring the NMR signal using either transducer 210 or 220.

Ultrasonic Drilling

Figure 11:
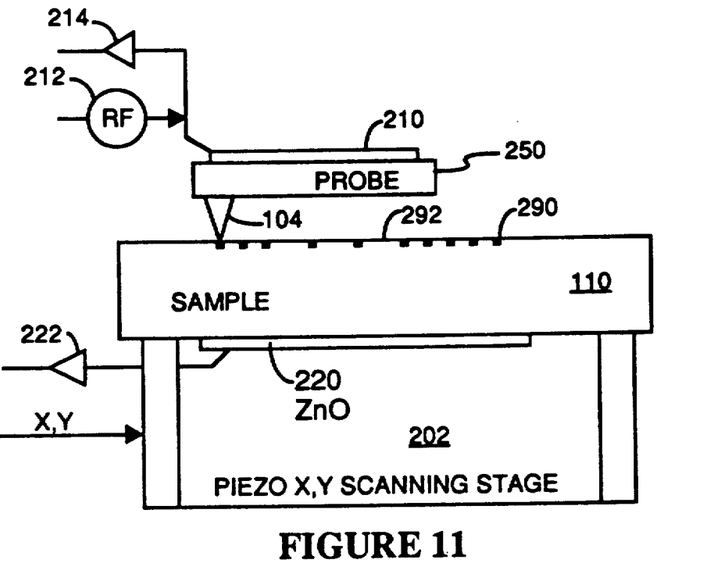
FIG. 11 is a block diagram of an acoustic microscope being used as a memory storage and retrieval apparatus.

Referring to FIG. 11, the acoustic microscope assembly of the present invention can also be used for ultrasonic drilling to modify the surface structure of an object in a controlled way. This technique could be used to scribe a line in a soft material such as the polymer films that are used for photoresist.

Very high frequency ultrasonic drilling can also be used to store information on a substrate, by deforming the substrate at selected positions so as to store data in binary form in the substrate. For example, at each position in an array of bit positions a deformation 290 could indicate a "1" while a lack of a deformation 292 could indicate a "0". Alternately, two distinct type of deformation could be used to distinguish "0" and "1" bits from each other as well as from empty space therebetween. The stored information is read by scanning the substrate while generating ultrasonic sound waves, and monitoring the reflected or transmitted acoustic signals so as determine which positions on a substrate have been deformed and which have not.

CANTILEVER MANUFACTURING PROCESS

Figure 12A:
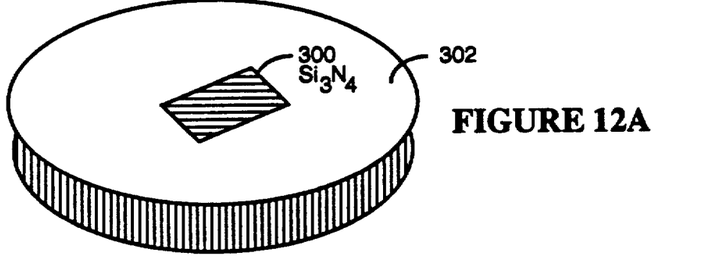
FIGS. 12A-12E depict a sequence of steps for manufacturing sharp silicon tips suitable for use in an acoustic microscope.
Figure 12B:
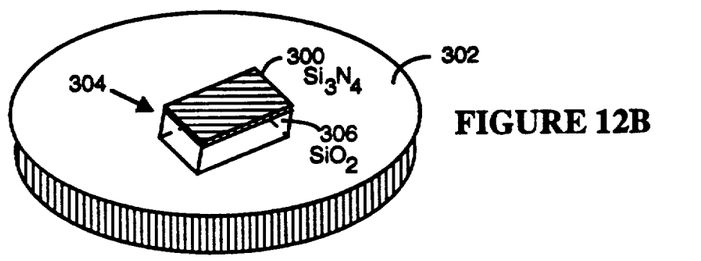
Figure 12C:
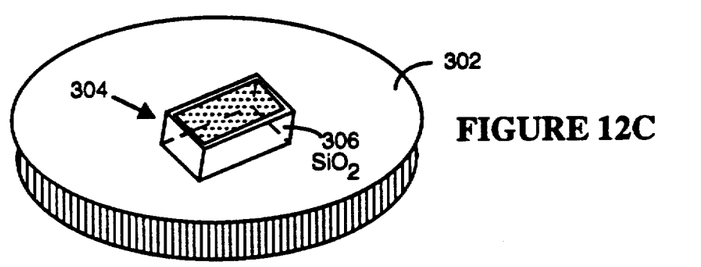
Figure 12D:
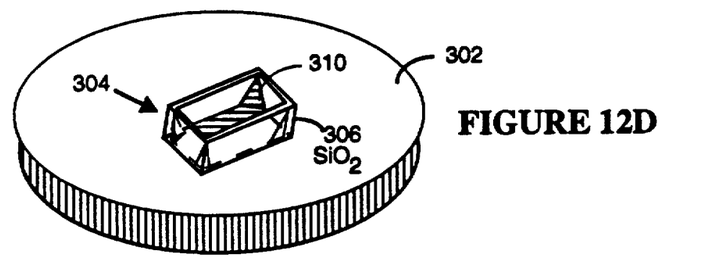
Figure 12E:
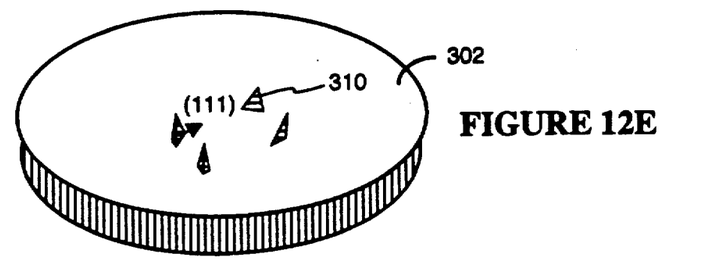

An essential feature of the microfabricated tip/transducer assembly is a sharp silicon tip. While there several known methods for making such tips, the one used in the preferred embodiment is a tetrahedral, single crystal silicon tip made as follows. Silicon nitride 300 is deposited and patterned on a (100) silicon substrate 302 to form a rectangular region of nitride with sharp corner points in the [110] direction (FIG. 12A). Then a silicon post 304 is etched into the substrate and has corner points in the [110] direction. Several thousand angstroms of oxide 306 are then grown at low temperatures (950 degrees Celsius) so that the sidewalls of the post are protected by oxide whereas the top of the post is still capped by nitride (FIG. 12B). The nitride cap is removed using a reactive ion etch (FIG. 12C). The exposed silicon in the center of the post is etched in an anisotropic silicon etchant such as EDP or KOH. Most of the post's interior is etched away during this step with the exception of small tetrahedral volumes 310 in the corners of the post. These tetrahedral volumes are not etched since there are bounded on their sides by oxide and on one face by a (111) crystallographic plane (FIG. 12D). To complete the process, the oxide sidewalls 306 are removed in an HF solution and the tips 310 are fully exposed (FIG. 12E).

Tips made in this way have radii of curvature typically less than 500 Angstroms and as low as 200 Angstroms. Even though the original silicon post has corners whose sharpness is limited by the resolution of lithography, the final sharpness is determined by the sharpening effect of the low temperature oxidation.

The ultrasonic transducer used on the cantilevers of the preferred embodiment is a sputtered ZnO film sandwiched between gold and titanium/gold electrodes, forming a 50×200 micron transducer that is resonant at a frequency of 175 MHz.

The substrate for the transducer is Corning 7740 glass, chosen to be compatible with silicon during a subsequent anodic bonding step.

The tip and transducer are aligned using a two sided aligner, then heated to 325 degrees Celsius on a hot plate and anodically bonded by applying −1500 to −2500 volts to the glass for 15 to 30 minutes.

Figure 13:
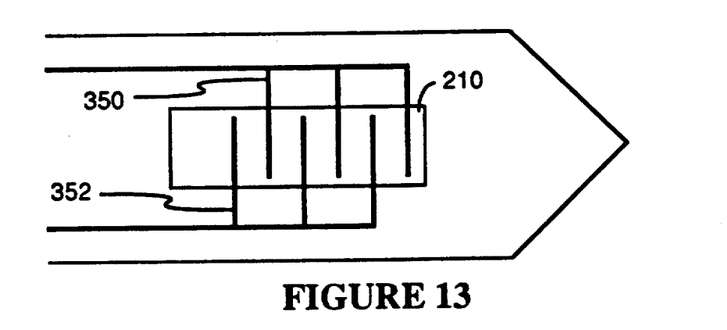
FIG. 13 shows a top view of a cantilever with interdigital metal fingers for contacting the ZnO thin film piezoelectric transducer thereon.

While the ZnO transducer 210 can be contacted by an ordinary wire, FIG. 13 shows a top view of a cantilever with interdigital metal fingers 350-352 for contacting the ZnO thin film piezoelectric transducer 210. The opposing fingers are spaced at half wavelength separations (based on the resonant frequency of the transducer 210), so that waves traveling down the cantilever from its tip produce two signals which are 180 degrees apart. Due to the very short wavelength of the ultrasonic sound waves being generated, this transducer 210 connection helps to produce a clean output signal.

Figure 14:
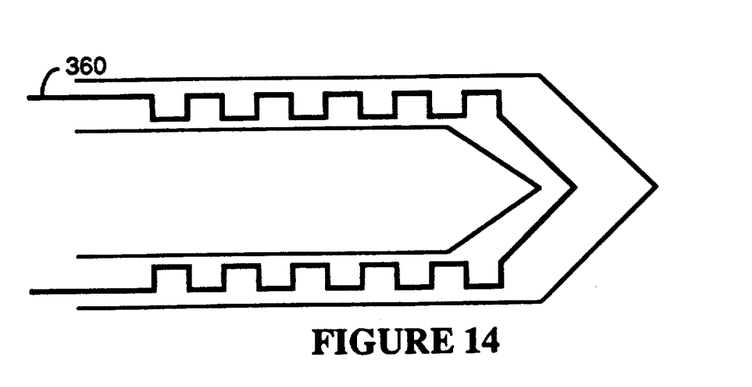
FIG. 14 shows a top view of a cantilever with a meander piezoresistor suitable for detecting deflection of the cantilever.

FIG. 14 shows a top view of a cantilever with a meander piezoresistor 360 suitable for detecting deflection of the cantilever by ultrasonic sound waves. Resistance of the piezoresistor changes with deflection of the cantilever, thereby enabling electronic detection of the cantilever's deflection without using the standard optics.

While the present invention has been described with reference to a few specific embodiments, the description is illustrative of the invention and is not to be construed as limiting the invention. Various modifications may occur to those skilled in the art without departing from the true spirirt and scope of the invention as defined by the appended claims.

What is claimed is:

1. An acoustic microscope assembly, comprising:
   a cantilever arm having an upper surface and a lower surface;
   a sharp tip on the lower surface of said cantilever arm;
   a piezoelectric thin film on at least a portion of the upper surface of said cantilever arm; and
   high frequency excitation means, coupled to said piezoelectric thin film, for applying an excitation signal having a frequency of at least 50 Megahertz to said piezoelectric thin film so as to generate high frequency acoustic signals;
   wherein said high frequency acoustic signals are transmitted through said sharp tip.

2. The acoustic microscope assembly of claim 1, wherein said piezoelectric thin film comprises a ZnO thin film.

3. The acoustic microscope assembly of claim 1, wherein said piezoelectric thin film is a ZnO thin film sandwiched between metal electrodes.

4. The acoustic microscope assembly of claim 1, further including acoustic signal receiving means for receiving said high frequency acoustic signals after said high frequency acoustic signals have interacted with a target object.

5. The acoustic microscope assembly of claim 1, further including acoustic signal receiving means, coupled to said piezoelectric thin film, for receiving said high frequency acoustic signals after said high frequency acoustic signals have been reflected by a target object.

6. The acoustic microscope assembly of claim 1, further including acoustic signal receiving means for receiving said high frequency acoustic signals after said high frequency acoustic signals have propagated through a target object.

7. The acoustic microscope assembly of claim 1, said high frequency excitation means applying a continuous wave signal to said piezoelectric thin film so as to generate a continuous wave high frequency acoustic signal;

said acoustic microscope assembly further including:
  acoustic signal receiving means for receiving said high frequency acoustic signals after said high frequency acoustic signals have interacted with a target object;
  positioning means for positioning said sharp tip with respect to said target object; and
  control means, coupled to said high frequency excitation means, said acoustic signal receiving means and said positioning means, for moving said sharp tip so as to scan said target object, and for measuring characteristics of said target object at various positions thereof by varying the frequency of said high frequency excitation signal while monitoring said acoustic signals received by said acoustic signal receiving means so as to measure resonant frequency of said transmitted high frequency acoustic signals.

8. The acoustic microscope assembly of claim 1, further including:
  positioning means for positioning said sharp tip with respect to a target object so as to leave a gap between said sharp tip and said target object;
  RF field generator means for generating an RF electrical field in said gap between said sharp tip and said target object;
  acoustic signal receiving means for receiving RF acoustic signals caused by said RF electrical field in said gap; and
  target object analysis means, coupled to said high frequency excitation means and said acoustic signal receiving means, for measuring characteristics of said target object by monitoring said RF acoustic signals received by said acoustic signal receiving means.

9. A method of performing acoustic microscopy, the steps of the method comprising:
  positioning, over a target object, a cantilever arm having an upper surface and a lower surface, said cantilever arm having a sharp tip on its lower surface and a piezoelectric thin film on at least a portion of its upper surface;
  applying to said piezelectric thin film an excitation signal having a frequency of at least 50 Megahertz so as to generate high frequency acoustic signals which are transmitted through said sharp tip; and
  receiving said high frequency acoustic signals after said high frequency acoustic signals have interacted with a target object.

10. The method of claim 9, wherein said piezoelectric thin film comprises a ZnO thin film.

11. The method of claim 9, wherein said receiving step includes receiving said high frequency acoustic signals after said high frequency acoustic signals have been reflected by a target object.

12. The method of claim 9, wherein said receiving step including receiving said high frequency acoustic signals after said high frequency acoustic signals have propagated through a target object.

13. The method of claim 9, wherein said applying step applies a continuous wave signal to said piezoelectric thin film so as to generate a continuous wave high frequency acoustic signal;

said method further including:
  moving said sharp tip so as to scan said target object; and
  measuring characteristics of said target object at various positions thereof by varying the frequency of said high frequency excitation signal while monitoring said received acoustic signals so as to measure resonant frequency of said transmitted high frequency acoustic signals.

14. A method of performing acoustic microscopy, the steps of the method comprising:
  positioning, over a target object, a probe having an upper surface and a lower surface, said probe having a sharp tip on its lower surface and a piezoelectric thin film on at least a portion of its upper surface; said probe being positioned with respect to said target object so as to leave a gap between said sharp tip and said target object;
  generating an RF electrical field in said gap between said sharp tip and said target object;
  receiving via said piezoelectric thin film RF acoustic signals caused by said RF electrical field in said gap; and
  measuring characteristics of said target object by measuring said received RF acoustic signals.

15. A method of performing acoustic microscopy, the steps of the method comprising:
  attaching a piezoelectric thin film to a target object;
  positioning, over said target object, a probe having a sharp tip on its lower surface; said probe being positioned with respect to said target object so as to leave a gap between said sharp tip and said target object;
  generating an RF electrical field in said gap between said sharp tip and said target object;
  receiving via said piezoelectric thin film RF acoustic signals caused by said RF electrical field in said gap; and
  measuring characteristics of said target object by measuring said received RF acoustic signals.

16. An acoustic microscope assembly, comprising:
  a probe having an upper surface and a lower surface;
  a sharp tip on the lower surface of said probe;
  a piezoelectric thin film on at least a portion of the upper surface of said probe;
  high frequency excitation means, coupled to said piezoelectric thin film, for applying an excitation signal having a frequency of at least 50 Megahertz to said piezoelectric thin film so as to generate high frequency acoustic signals; wherein said high frequency acoustic signals are transmitted through said sharp tip;
  acoustic signal receiving means for receiving said high frequency acoustic signals after said high frequency acoustic signals have interacted with a target object;
  positioning means for positioning said sharp tip with respect to said target object; and
  control means, coupled to said high frequency excitation means, said acoustic signal receiving means and said positioning means, for moving said sharp tip so as to scan said target object, and for measuring characteristics of said target object at various positions thereof by varying the frequency of said high frequency excitation signal while monitoring said acoustic signals received by said acoustic signal receiving means so as to measure resonant frequency of said transmitted high frequency acoustic signals.

17. The acoustic microscope assembly of claim 16, wherein said piezoelectric thin film comprises a ZnO thin film.

18. The acoustic microscope assembly of claim 16, further including acoustic signal receiving means, coupled to said piezoelectric thin film, for receiving said high frequency acoustic signals after said high frequency acoustic signals have been reflected by a target object.

19. The acoustic microscope assembly of claim 16, further including acoustic signal receiving means for receiving said high frequency acoustic signals after said high frequency acoustic signals have propagated through a target object.

20. An acoustic microscope assembly comprising: a probe having an upper surface and a lower surface;
   a sharp tip on the lower surface of said probe;
   a piezoelectric thin film on at least a portion of the upper surface of said probe;
   high frequency excitation means, coupled to said piezoelectric thin film, for applying an excitation signal having a frequency of at least 50 Megahertz to said piezoelectric thin film so as to generate high frequency acoustic signals; said high frequency excitation means applying a continuous wave signal to said piezoelectric thin film so as to generate a continuous wave high frequency acoustic signal; wherein said high frequency acoustic signals are transmitted through said sharp tip;
   acoustic signal receiving means for receiving said high frequency acoustic signals after said high frequency acoustic signals have interacted with a target object;
   positioning means for positioning said sharp tip with respect to said target object; and
   control means, coupled to said high frequency excitation means, said acoustic signal receiving means and said positioning means, for moving said sharp tip so as to scan said target object, and for measuring characteristics of said target object at various positions thereof by varying the frequency of said high frequency excitation signal while monitoring said acoustic signals received by said acoustic signal receiving means so as to measure resonant frequency of said transmitted high frequency acoustic signals.

21. A method of performing acoustic microscopy, the steps of the method comprising:
   positioning, over a target object, a probe having an upper surface and a lower surface, said probe having a sharp tip on its lower surface and a piezoelectric thin film on at least a portion of its upper surface;
   applying to said piezoelectric thin film on excitation signal having a frequency of at least 50 Megahertz so as to generate high frequency acoustic signals which are transmitted through said sharp tip;
   moving said sharp tip so as to scan said target object;
   measuring characteristics of said target object at various positions thereof by varying the frequency of said high frequency excitation signal while monitoring said acoustic signals received by said acoustic signal receiving means so as to measure resonant frequency of said transmitted high frequency acoustic signals; and
   receiving said high frequency acoustic signals after said high frequency acoustic signals have interacted with a target object.

22. The method of claim 21, wherein said applying step applies a continuous wave signal to said piezoelectric thin film so as to generate a continuous wave high frequency acoustic signal.

* * * * *

UNITED STATES PATENT AND TRADEMARK OFFICE
CERTIFICATE OF CORRECTION

PATENT NO. : 5,319,977

DATED : June 14, 1994

INVENTOR(S) : Quate et al.

It is certified that error appears in the above-indentified patent and that said Letters Patent is hereby corrected as shown below:

Column 1, after title insert --This invention was made with Government support under contract N00014-90-J-1635 awarded by the Department of the Navy. The Government has certain rights in this invention.

Signed and Sealed this

Sixteenth Day of May, 1995

Attest:

BRUCE LEHMAN

Attesting Officer

Commissioner of Patents and Trademarks